United States Patent [19]

Neumann

[11] Patent Number: 5,440,870
[45] Date of Patent: Aug. 15, 1995

[54] METHOD AND APPARATUS OF MONITORING THE QUALITY OF A FALSE TWIST TEXTURED YARN

[75] Inventor: Bernd Neumann, Radevormwald, Germany

[73] Assignee: Barmag AG, Remscheid, Germany

[21] Appl. No.: 818,511

[22] Filed: Jan. 9, 1992

[30] Foreign Application Priority Data

Jan. 17, 1991 [DE] Germany ............. 41 01 189.9
Mar. 13, 1991 [DE] Germany ............. 41 07 951.5

[51] Int. Cl.⁶ ................ D01H 7/92; D01H 13/22
[52] U.S. Cl. ............................ 57/265; 57/81; 57/284; 73/828; 340/677
[58] Field of Search ............. 57/264, 265, 284, 81; 340/677, 683; 73/828, 160

[56] References Cited

U.S. PATENT DOCUMENTS 4,720,702 1/1988 Martens .................... 57/81
5,018,390 5/1991 Muller .................... 28/187

FOREIGN PATENT DOCUMENTS 1135384 11/1982 Canada .
0406736 1/1991 European Pat. Off. .
0439183 7/1991 European Pat. Off. .

Primary Examiner—Joseph J. Hail, III
Attorney, Agent, or Firm—Bell, Seltzer, Park & Gibson

[57] ABSTRACT

A method and apparatus for monitoring the quality of the yarn processed on a false twist texturing machine is disclosed, and which includes sensing the tension of the advancing yarn at a location immediately downstream of the false twist unit, and determining the coefficient of variation of the sensed tension. An error signal is generated whenever the coefficient of variation exceeds a predetermined upper limit and whenever the coefficient of variation drops below a predetermined lower limit. Also, an alarm signal is generated whenever the error signal exceeds the predetermined upper limit for a predetermined time, and whenever the error signal drops below the predetermined lower limit for a predetermined time, and the alarm signals are counted so as to provide an indication of the quality of the yarn.

13 Claims, 3 Drawing Sheets

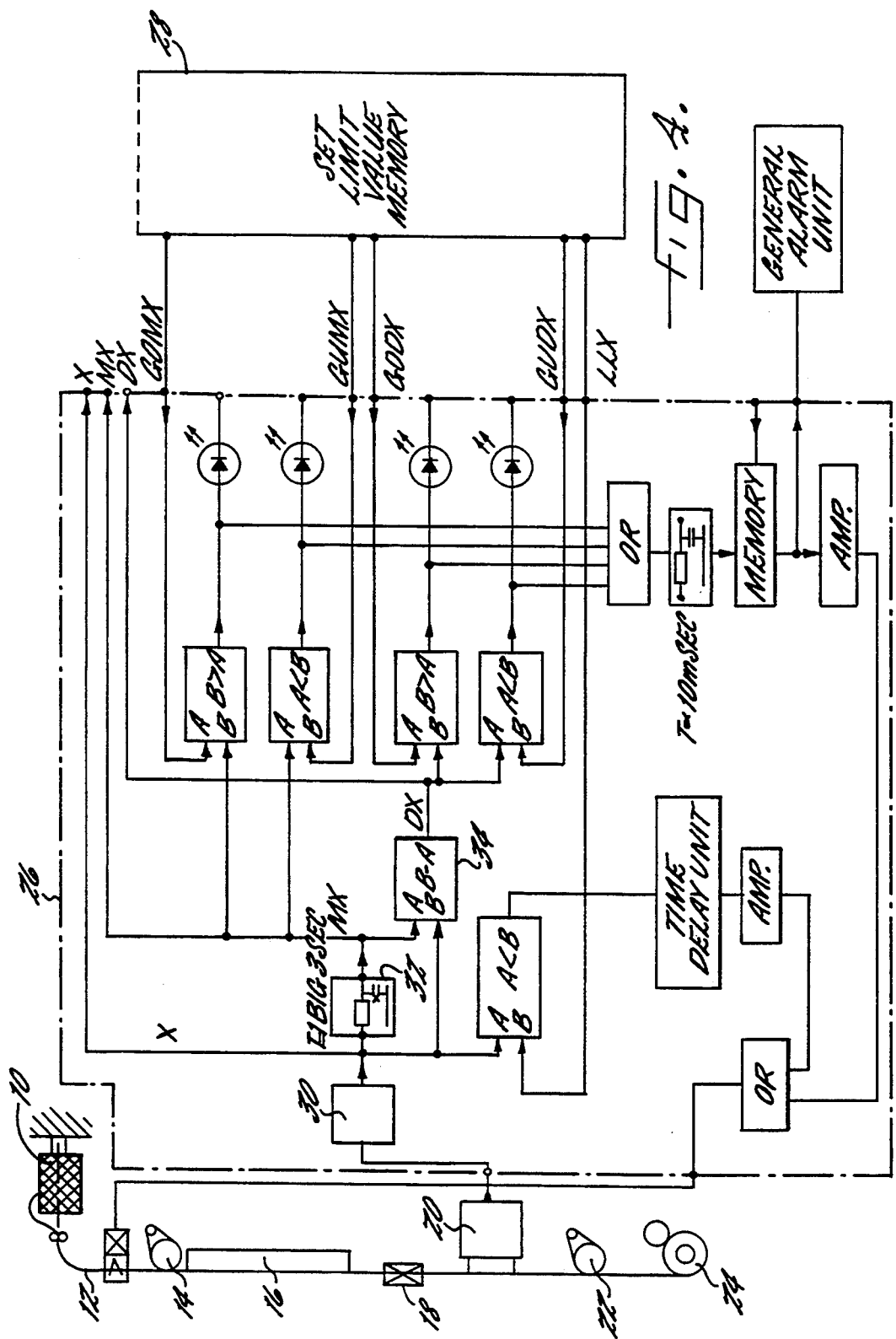

METHOD AND APPARATUS OF MONITORING THE QUALITY OF A FALSE TWIST TEXTURED YARN

BACKGROUND OF THE INVENTION

The present invention relates to a method and apparatus for monitoring the crimp quality of a synthetic filament yarn produced by false twist texturing process.

A method of monitoring the tension of a yarn advancing between the false twisting unit and the delivery system in the texturing zone of a multi-position false twist crimping machine, in which a mean value signal is continuously formed, is known from U.S. Pat. No. 4,720,702 to Martens. In that known method, use is made of the fact that the yarn tension between the false twisting unit and the delivery system of the texturing zone allows essential conclusions to be drawn as to the control of the process during the texturing and the quality of the yarn produced. More particularly, the yarn tension is monitored such that, on the one hand, the minimum and maximum values of the tension do not leave a certain range on either side of the continuously determined mean value, and such that, on the other hand, the continuously determined mean value of the yarn tension does not leave a certain predetermined range.

It is an object of the present invention to monitor the intensity and uniformity of the twisting process in the texturizing zone and also to monitor and record the uniformity of the setting of the twist attained in the advancing yarn by a thermal setting process, these parameters directly reflecting the results of the texturing process.

SUMMARY OF THE INVENTION

The above and other objects and advantages of the present invention are achieved in the embodiment illustrated herein by the provision of a method and apparatus which includes the steps of continuously sensing the tension of the advancing yarn, while continuously determining the coefficient of variation of the sensed yarn tension, and generating an error signal whenever at least one of the following conditions is present: (1) the coefficient of variation exceeds a predetermined upper limit, and (2) the coefficient of variation drops below a predetermined lower limit.

In the preferred embodiment, the step of generating an error signal includes generating the signal whenever the coefficient of variation exceeds the upper limit and whenever it falls below the lower limit. Also, an alarm signal may be generated whenever the error signal, which is generated whenever the coefficient of variation falls outside the range between the upper and lower limits, continues for a predetermined time, and these alarm signals may be counted to provide an indication of the quality of the yarn.

The present invention makes it possible to obtain a direct indication as to certain criteria of the yarn being processed irrespective of the denier. For example, the falling below the lower limit value of the coefficient of variation is not necessarily an indication of a particularly smooth and hence advantageous yarn path, but rather an indication of the fact that inadequate twist is imparted.

From a technological viewpoint, it is advantageous to emit the error signals as short-term alarm signals. To avoid the influence of irrelevant disturbances, these alarm signals are counted, and only the exceeding of predetermined sums is used for intervening in the process or emitting quality classification signals.

It has been found that falling below the lower limit value on the one hand and the exceeding of the upper limit value on the other hand give a warning of different errors. The exceeding of the upper limit value indicates primarily that the setting of the twist by the heat setting process is out of order. This may be based upon contamination of the heating plate, unsatisfactory guidance of the yarn in the heating plate, yarn defects, or irregular moistening of the yarn advancing from its supply package. A drop below the lower limit value typically indicates an inadequate impartation of twist. The cause may be that the false twister is out of operation, that the yarn is not properly guided in the false twister, and that the false twister has defective friction elements or is contaminated.

For the above reason, the alarm signals are preferably counted separately, and a warning thereof is given after exceeding the upper limit value or falling below the lower limit value.

BRIEF DESCRIPTION OF THE DRAWINGS

Some of the objects and advantages of the present invention having been stated, others will appear as the description proceeds when considered in conjunction with the accompanying schematic drawings, in which

FIG. 4 is a schematic diagram of a false twisting apparatus and portion of the control circuitry in accordance with the present invention.

DETAILED DESCRIPTION OF THE PREFERRED EMBODIMENT

Figure 1:
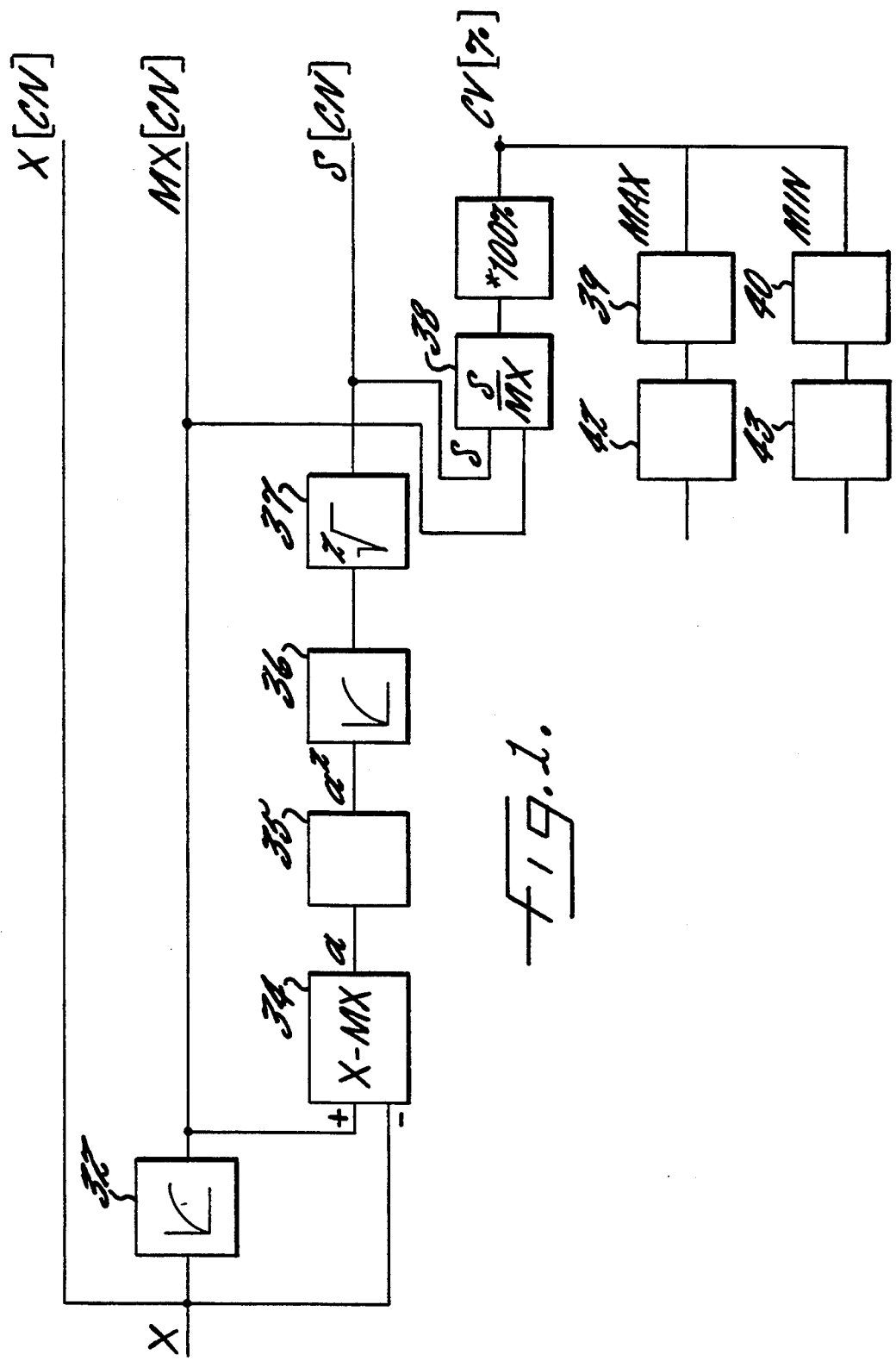
FIG. 1 is a schematic representation of a portion of the signal processing circuit of the present invention.

Referring more particularly to the drawing, FIG. 4 schematically illustrates a yarn false twisting apparatus and a portion of the control circuitry of the present invention. Further details of the apparatus illustrated in FIG. 4 may be obtained from the U.S. Patent to Martens, U.S. Pat. No. 4,720,702, the disclosure of which is expressly incorporated herein by reference.

As illustrated in FIG. 4, each working position of a false twist crimping machine is provided with a supply package 10 from which a yarn 12 to be processed is withdrawn by means of a first delivery system 14. In the illustrated embodiment, a yarn cutter 15 is arranged before the delivery roll 14. After the first delivery roll 14, the yarn 12 travels along a heating plate 26, which is straight in the illustrated embodiment but which may be curved, and which is heated to, for example, 200° C. After the heating plate 16, the yarn 12 advances through a cooling zone and then through a false twister 18 of conventional design. The false twister 18 is followed by a yarn tension measuring instrument 20 which permits the yarn tension to be continuously sensed. Subsequently, the yarn 12 is withdrawn by a second or delivery roll 22, and advanced either to a further heating system or, as shown, directly to a takeup where it is wound into a package 24.

The yarn sensor 20 generates an output signal which in its magnitude and shape or slope is representative of the yarn tension and its fluctuations between the false twister 18 and the delivery roll 22. This signal is supplied to a circuit 26 which is within the dash-dotted lines in FIG. 4, and which receives predetermined limit values as comparative values from a limit value memory 28 which will be described below. Whereas each yarn sensor 20 of each position of a texturing machine is associated with a circuit 26, one limit value memory 28 is associated with a group of texturing positions of a multiposition texturing machine.

The output signal associated with the yarn tension between the false twister 18 and the delivery roll 22 is amplified by an amplifier 30 to produce an electrical voltage signal indicated at X (the corresponding signal is indicated at U in U.S. Pat. No. 4,720,702). From the voltage X, a filter 32 forms a mean value MX. The measured signal X and its continuously formed mean value MX are supplied to a differential amplifier 34 in which the difference between measured value and mean value is formed. Reference may be made to the above cited U.S. Pat. No. 4,720,702 for a more detailed description of the other elements of circuit illustrated in FIG. 4.

FIG. 1 shows the further processing of the measured value X and its mean value MX, in accordance with the invention. More particularly, the output signal a of the differential amplifier 34 is supplied to a squaring element 35. A further filtering in filter 36 of the squared signal $a^2$, and a determination of the square root from the filtered signal at 37 permit the standard deviation S to be determined. From the standard deviation S the quotient with the mean value MX is then determined in the computing element 38 and output as the coefficient of variation or respectively as the relative standard deviation CV in the form of a percentage figure. In comparator elements 39 and 40, this continuously formed coefficient of variation CV is continuously compared with a predetermined maximum value and a predetermined minimum value. The output signals are added in counters 42 and 43 respectively, the output sums of which indicate the aforementioned errors.

As will be apparent from FIG. 1, the standard deviation S may be defined as the square root of the mean square of the deviations of the signal X from the mean signal MX. Also, the coefficient of variation CV may be defined as the ratio of the standard deviation S to the mean signal MX.

Figure 2:
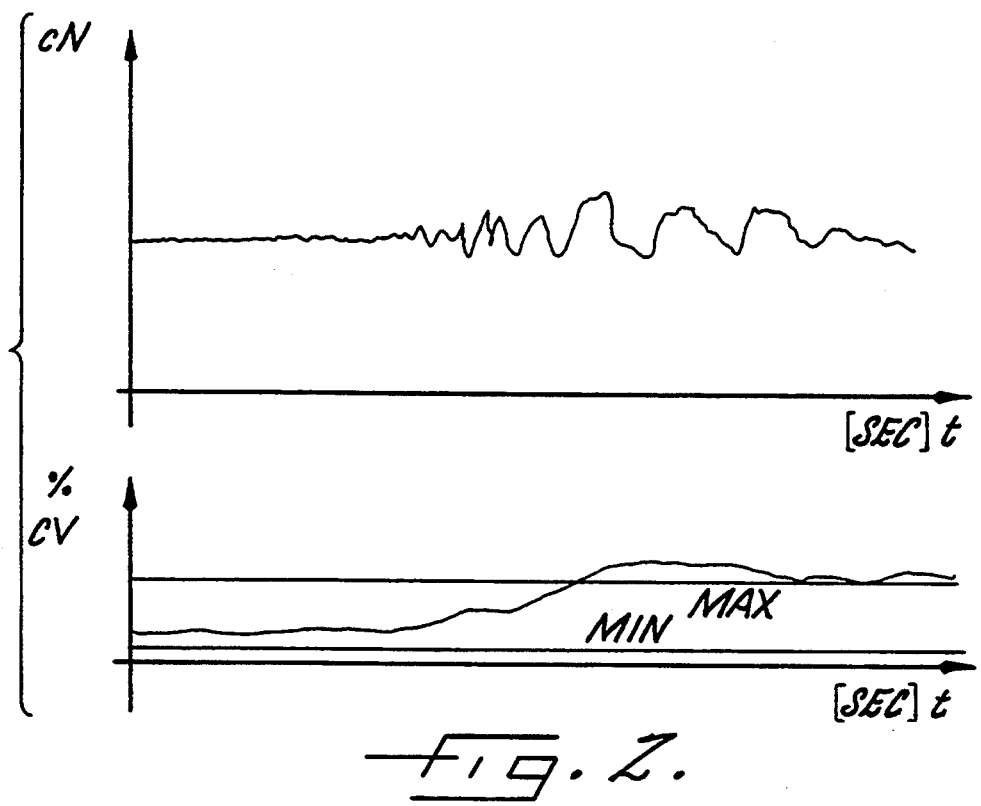
FIGS. 2 and 3 are diagrams illustrating the values of the sensed tension and the coefficient of variation versus time, in accordance with the present invention.
Figure 3:
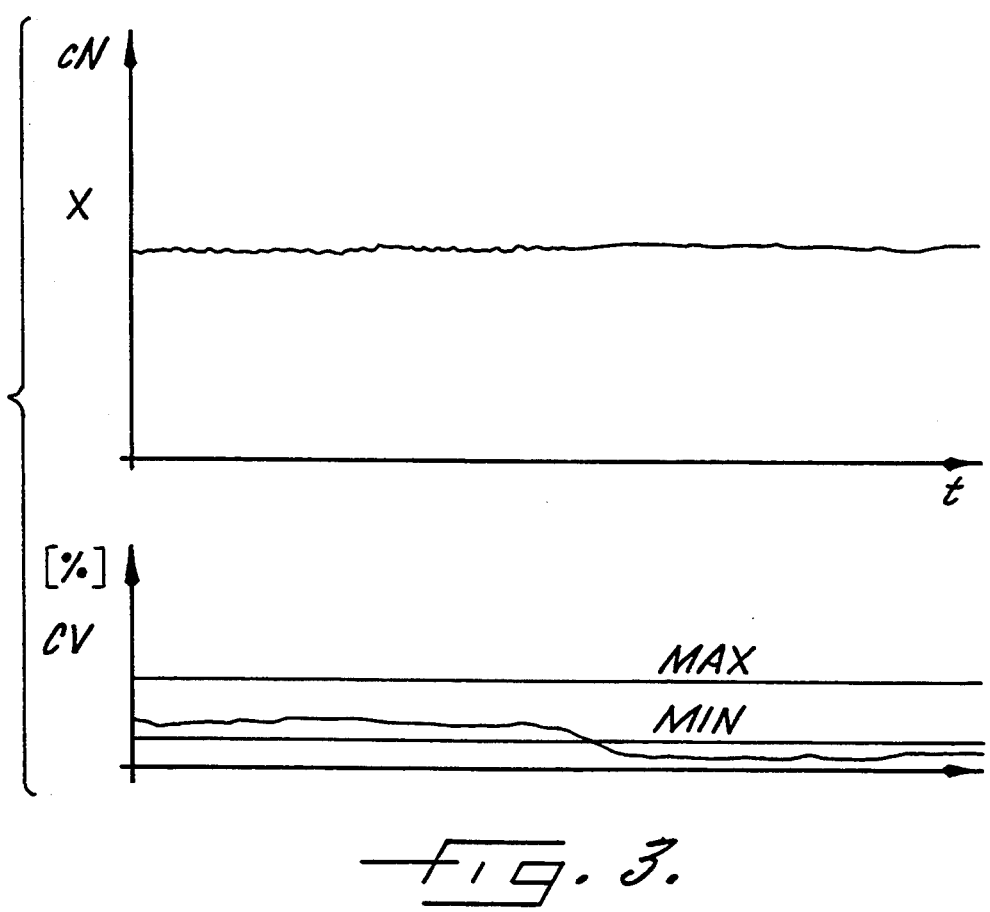

FIGS. 2 and 3 represent a measuring record of the continuous yarn tension signal X, as well as a graphic record of the continuous coefficient of variation CV derived therefrom. FIG. 2 illustrates a phase with a very unsteady curve of the yarn tension or yarn tension signal X respectively. In this graph the upper limit of the CV value is exceeded and consequently output as an error signal.

FIG. 3 shows a phase with a periodically flawless yarn tension signal X. In this graph, the curve falls below the lower limit value of the coefficient of variation. The nature of defects which are present in this instance have been described above.

It should be pointed out that the summation of the error signals includes not only the occurrence of the error signal itself, but also the duration of the occurring error signal. This is achieved in that the respective error signal is repeated in certain, fixedly input time intervals as long as the error is present, i.e., whenever the error signal is generated because the coefficient of variation CV is exceeding or falling below the limit values. Stated in other words, an alarm signal is generated: (i) whenever the error signal which results whenever the coefficient of variation CV exceeds the predetermined upper limit continues for a predetermined time, and (ii) whenever the error signal which results whenever the coefficient of variation CV drops below the predetermined lower limit continues for a predetermined time. These alarm signals are counted so as to provide an indication of the quality of the yarn. U.S. Pat. No. 5,018,390 to Muller contains a further description of a similar counting operation, and the disclosure of such patent is expressly incorporated by reference.

In the drawings and specification, there has been set forth a preferred embodiment of the invention, and although specific terms are employed, they are used in a generic and descriptive sense only and not for purposes of limitation.

That which is claimed is:

1. A method of monitoring the quality of an advancing yarn and comprising the steps of continuously sensing the tension of the advancing yarn, while continuously determining the coefficient of variation of the sensed yarn tension and including the steps of:
(a) deriving a signal representative of the tension of the advancing yarn;
(b) filtering said tension signal to derive a mean value thereof;
(c) deriving a signal representative of the difference between said mean value and said tension signal;
(d) squaring said difference signal;
(e) filtering said squared signal;
(f) deriving the square root of said filtered squared signal; and
(g) deriving the quotient of said square root divided by said mean value, and generating an error signal whenever at least one of the following conditions is present: (1) the coefficient of variation exceeds a predetermined upper limit, and (2) the coefficient of variation drops below a predetermined lower limit.

2. The method as defined in claim 1 wherein the step of generating an error signal includes generating an error signal whenever the coefficient of variation exceeds the predetermined upper limit or whenever the coefficient of variation drops below the predetermined lower limit.

3. The method as defined in claim 2 wherein the step of generating an error signal further includes generating an alarm signal: (i) whenever the error signal generated when the coefficient of variation exceeds the predetermined upper limit continues for a predetermined time, or (ii) whenever the error signal generated when the coefficient of variation drops below the predetermined lower limit continues for a predetetermined time, and counting the alarm signals so as to provide an indication of the quality of the yarn.

4. The method as defined in claim 3 wherein the step of counting the alarm signals includes separately counting the alarm signals generated by the error signals generated when the coefficient of variation exceeds the predetermined upper limit or the alarm signals generated by the error signals generated when the coefficient of variation drops below the predetermined lower limit.

5. A method of false twisting a yarn and comprising the steps of advancing the yarn along a path of travel while serially heating the yarn, cooling the yarn, false twisting the yarn, and then winding the yarn into a package, continuously sensing the tension of the advancing yarn at a location along the path of travel between the location at which the false twist is applied and the location at which the yarn is wound into a package, while continuously determining the coefficient of variation of the sensed yarn tension and including the steps of:

(a) deriving a signal representative of the tension of the advancing yarn;

(b) filtering said tension signal to derive a mean value thereof;

c) deriving a signal representative of the difference between said mean value and said tension signal;

(d) squaring said difference signal;

(e) filtering said squared signal;

(f) deriving the square roof of said filtered squared signal; and g) deriving the quotient of said square root divided by said mean value, and generating an error signal whenever the coefficient of variation exceeds a predetermined upper limit or whenever the coefficient of variation drops below a predetermined lower limit.

6. The method as defined in claim 5 wherein the step of generating an error signals includes generating an alarm signal: (i) whenever the error signal generated when the coefficient of variation exceeds the predetermined upper limit continues for a predetermined time, or (ii) whenever the error signal generated when the coefficient of variation drops below the predetermined lower limit continues for a predetermined time, and counting the alarm signals so as to provide an indication of the quality of the yarn.

7. The method as defined in claim 6 wherein the step of counting the alarm signals includes separately counting the alarm signals generated by the error signals generated when the coefficient of variation exceeds the predetermined upper limit or the alarm signals generated by the error signals generated when the coefficient of variation drops below the predetermined lower limit.

8. An apparatus for monitoring the tension of an advancing yarn comprising sensor means for continuously sensing the tension of the advancing yarn and producing a continuous output signal representative of the sensed tension, first circuit means operatively connected to said sensor means for continuously determining the coefficient of variation of said output signal, and comprising (a) means for deriving a signal representative of the tension of the advancing yarn;

(b) means for filtering said tension signal to derive a mean value thereof;

(c) means for deriving a signal representative of the difference between said mean value and said tension signal;

(d) means for squaring said difference signal;

(e) means for filtering said squared signal;

(f) means for deriving the square roof of said filtered squared signal; and (g) means for deriving the quotient of said square root divided by said mean value; and second circuit means for generating an error signal whenever at least one of the following conditions is present: (1) the coefficient of variation exceeds a predetermined upper limit, and (2) the coefficient of variation drops below a predetermined lower limit.

9. The apparatus as defined in claim 8 wherein said second circuit means includes means for generating an error signal whenever the coefficient of variation exceeds the predetermined upper limit or whenever the coefficient of variation drops below the predetermined lower limit.

10. The apparatus as defined in claim 9 wherein said second circuit means further includes means for generating an alarm signal: (i) whenever the error signal generated when the coefficient of variation exceeds the predetermined upper limit continues for a predetermined time, or (ii) whenever the error signal generated when the coefficient of variation drops below the predetermined lower limit continues for a predetermined time, and means for counting the alarm signals so as to provide an indication of the quality of the yarn.

11. The apparatus as defined in claim 10 wherein the means for counting the alarm signals includes means for separately counting the alarm signals generated by the error signals generated when the coefficient of variation exceeds the predetermined upper limit, or the alarm signals generated by the error signals generated when the coefficient of variation drops below the predetermined lower limit.

12. The apparatus as defined in claim 8 further comprising means for advancing the yarn along a path of travel while serially heating the yarn, cooling the yarn, false twisting the yarn, and then winding the yarn into a package, and wherein said sensor means is positioned between the location at which the yarn is false twisted and the location at which the yarn is wound into a package.

13. The apparatus of claim 8, wherein said means for deriving a signal representative of the difference between said mean value and said tension signal comprises a differential amplifier.

* * * * *